United States Patent [19]

Cooper

[11] Patent Number: 4,464,027
[45] Date of Patent: Aug. 7, 1984

[54] BINOCULAR TRAINER

[76] Inventor: Clifford W. Cooper, P.O. Box 264, Santa Cruz, Calif. 95061

[21] Appl. No.: 460,678

[22] Filed: Sep. 19, 1983

Related U.S. Application Data

[63] Continuation-in-part of Ser. No. 291,387, Dec. 7, 1982.

[51] Int. Cl.³ .............................................. A61B 3/08
[52] U.S. Cl. ................................. 351/203; 128/76.5; 351/201
[58] Field of Search ................ 351/203, 201; 434/178, 434/247, 258, 262; 128/25 A, 76.5

[56] References Cited

U.S. PATENT DOCUMENTS

| | | | |
|---|---|---|---|
| 1,702,700 | 2/1929 | Martin | 351/203 |
| 2,263,190 | 11/1941 | Quinan | 351/203 |
| 3,875,934 | 4/1975 | Sadanaga | 351/203 |
| 4,035,066 | 7/1977 | Slomski | 351/201 |
| 4,260,226 | 4/1981 | Ghahramani | 351/201 |
| 4,294,522 | 10/1981 | Jacobs | 351/203 |
| 4,408,846 | 10/1983 | Balliet | 351/203 |

Primary Examiner—William H. Grieb
Attorney, Agent, or Firm—David E. Newhouse

[57] ABSTRACT

A binocular vision training device is described which includes a lighted enclosure having a pair of viewing ports through which a patient can view the interior of the enclosure, each eye being in registry with one of the ports. Within the enclosure, there are two stationary vertical posts oriented and aligned in a vertical plane bisecting the distance between the viewing ports, and a post movable in the same vertical plane back and forth from a position directly above one of the stationary posts to a position directly above the remaining stationary post. The movement of the latter post exercises critical muscle culture and the mental processes necessary for proper binocular perception of fine visual stimulus patterns.

12 Claims, 5 Drawing Figures

U.S. Patent   Aug. 7, 1984   Sheet 1 of 2   4,464,027

BINOCULAR TRAINER

This application is a continuation-in-part of application Ser. No. 06/291,387 filed with the U.S. Patent Office on Dec. 7, 1982, entitled "BINOCULAR TRAINER".

BACKGROUND OF THE INVENTION

When reading a book, the eyes of the reader are focused on the plane of the page, i.e. the image plane. The focus of a reader can deviate small amounts from exact focus on the image plane; however, larger deviations result in a loss of focus on the image plane.

In terms of reading, the loss of focus frequently results in loss of information. In particular, when a reader's eyes are focused on an image plane, visual information in plane is readily "transducible", the image falling on the retina being well defined. Accordingly, the retinal cells are optimally stimulated and the symbolic structure of the visual stimulus is optimally transmitted to the brain. However, the visual stimulus of an image perceived and momentarily stored by the retinal cells rapidly decays under conditions of incomplete "transduction". Such incomplete transduction occurs when the reader's eyes deviate from a particular image plane, causing a loss of focus in that plane.

Such loss of focus occurs whenever one of a reader's eyes drifts or changes focus, the other eye automatically adjusting or changing its focus as well. This is called "compensation" and it affects the binocular focal length of the eyes. The binocular focal length of the eyes is the distance between the plane of the eyes and the plane on which both eyes are focused. The amount of compensation is a function of both the amount of angular drift of a particular eye and the time over which that drift occurs. Usually, a larger drift occurs over a longer period of time, resulting in a greater compensatory change in the binocular focal length of the eyes. If the angular drift is sufficiently great, there is a complete loss of focus in the original image plane, resulting in a loss of stimulus data stored in the retinal cells.

If the above phenomena occurs when reading a book, the reader must re-focus on the image plane of the page. Upon restoring focus to the plane of the page, the reader frequently has trouble remembering where he was because the stimulus providing for such was lost with the loss of focus. This phenomenon can be very frustrating to readers and particularly to young persons just learning to read.

For example, if the left eye of the reader travels some angular distance to its left due to slack in the six pairs of extrensic eye muscles that control its horizontal movement, the right eye immediately compensates for the change in focal length by moving its position to the right. Focus is restored, but on a plane different from that of the original image plane, i.e., that of the plane of the page being read. The information on the image plane is not available, it being out of focus. Accordingly, that portion of the information from the image plane which had not been received and transmitted by the optic nerve to the brain is lost. Accordingly, after refocusing on the original image plane, the reader must search for his last-remembered reference point on the original image plane. This phenomenon is commonly termed "losing one's place" while reading.

Young children frequently utilize visual aids in maintaining their binocular focus on the plane of a page being read. For example, a child frequently uses his finger to maintain his position on a page.

SUMMARY OF THE INVENTION

A device for testing, exercising, and increasing binocular vision is described which includes an enclosure with two viewports positioned to register with a viewer's eyes, two stationary posts aligned in a spaced-apart relationship in a vertical plane bisecting the distance between the viewing ports, a movable post movable in the same vertical plane back and forth from a position directly above one of the stationary posts to a position directly above the other stationary post, and means for uniformally illuminating the interior of the enclosure. The exterior of the enclosure may further include a chin rest below the viewing ports such that a viewer may rest his chin in order to steady the plane of his eyes while viewing the interior of the enclosure. A viewer focuses on the movable post as its position is moved from one directly above one of the stationary posts to one directly above the other post. The muscles controlling the eyes are exercised by maintaining focus on the post as it moves. The mental processes for maintaining proper binocular vision are exercised by ignoring "dual images" of the stationary posts.

DESCRIPTION OF PREFERRED EMBODIMENTS

Figure 1:
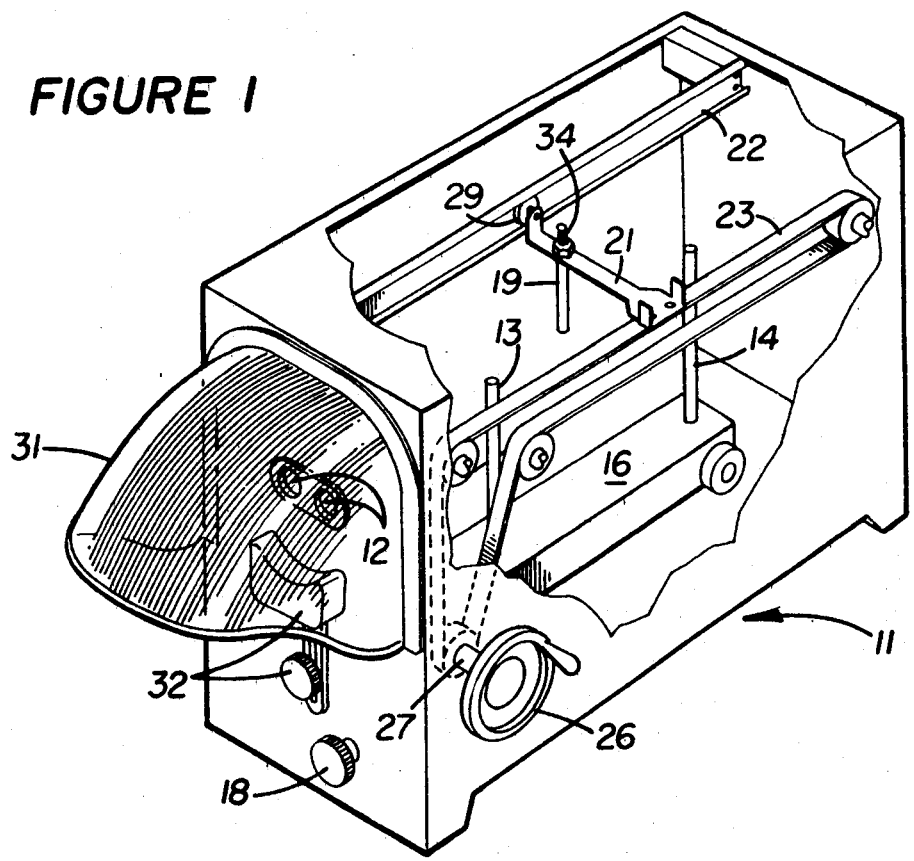
FIG. 1 is a perspective cutaway view of the binocular vision training device.
Figure 2:
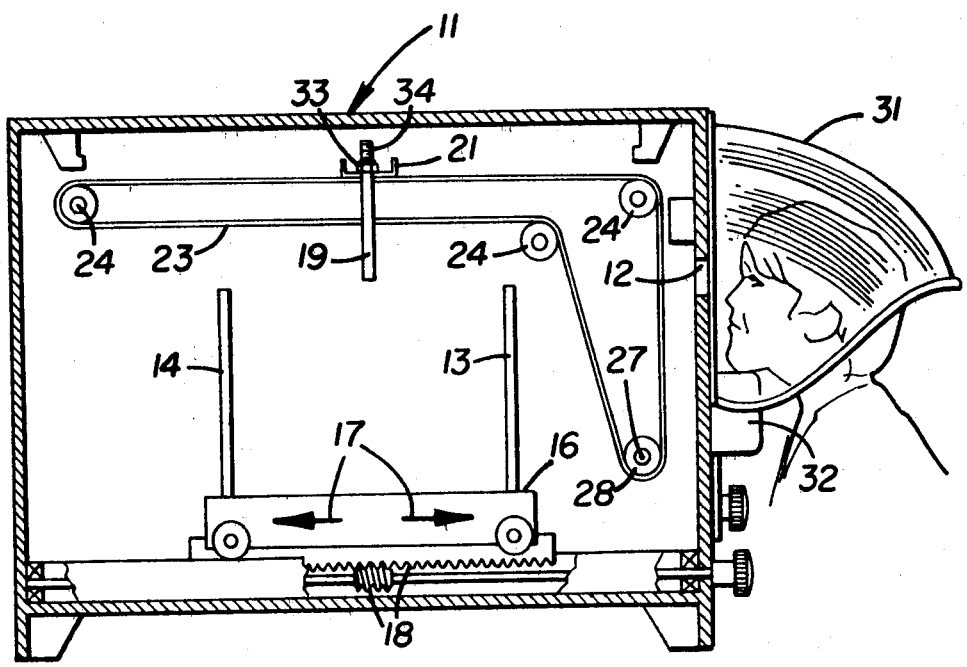
FIG. 2 is a cross-sectional elevated view of the binocular vision training device.

Referring to FIGS. 1 and 2, the binocular vision training device includes an illuminated enclosure 11, a pair of viewing ports or aperatures 12, through which a patient can view the interior of the enclosure 11. Within the enclosure 11, there are two stationary vertical posts 13 and 14 oriented and aligned in a vertical plane bisecting the distance between the viewing ports 12. The vertical posts 13 and 14 are mounted on a carriage 16 which can be moved toward and away from the viewing ports as indicated by the arrows 17. A simple rack and pinion mechanism 18 is shown in FIG. 2 is shown for moving the carriage 16 back and forth.

Also within the enclosure 11 is a movable post 19 positioned above the stationary vertical posts 13 and 14 in the same vertical plane. The movable post depends from a horizontal support member 21 which is supported by a channel 22 on one side of the enclosure and a belt 23 on the opposite side of the enclosure 11. The belt 23 is strung around several pulleys 24. The belt 23 is moved by rotating a hand crank 26 outside of the enclosure 11. The hand crank 26 is keyed to a shaft 27 extending through the wall of the enclosure 11 and keyed to one of the pulleys 28. The horizontal support member 21 is positively secured to the belt. The remaining end of the horizontal support member 21 terminates in a small wheel 29 which is received in and supported by the channel element 22.

The posts 13, 14 and 19 should have a diameter ranging from a minimum of 32 millimeters to a maximum of 154 millimeters. The stationary posts should be positioned approximately 30 to 40 centimeters apart. The interior of the enclosure should be illuminated by indirect electrical lighting (not shown in the figures). Also, the interior of the enclosure 11 should be painted a uniform color so as to minimize distraction due to its internal working components. In fact, it may be preferable to include interior walls on within the enclosure to shield the internal mechanisms from view by a person viewing the interior of the enclosure 11 through the viewing aperatures 12.

In operation, a patient views the interior of the device through the aperatures 12. He or another person moves the movable post 19 from a position directly above, for example, the front vertical post 13 to a position directly above the back vertical post 14. The patient maintains his focus on the movable post 19. As the post moves from a position directly above vertical post 13, the binocular focal plane of the patient's eyes moves with the movable post, and, assuming the patient maintains his focus on the movable post, dual images of the stationary posts 13 and 14 will be perceivable.

Figure 3A:
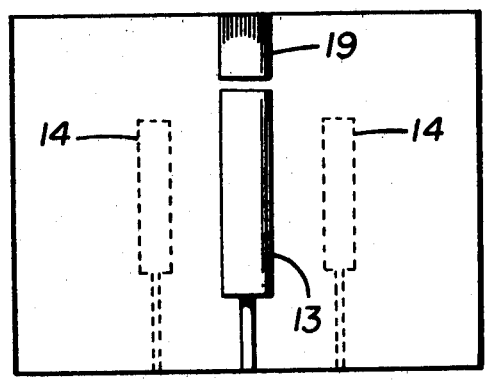
FIGS. 3(a), 3(b), and 3(c) illustrate the various images that a viewer may perceive while utilizing the binocular vision training device.
Figure 3B:
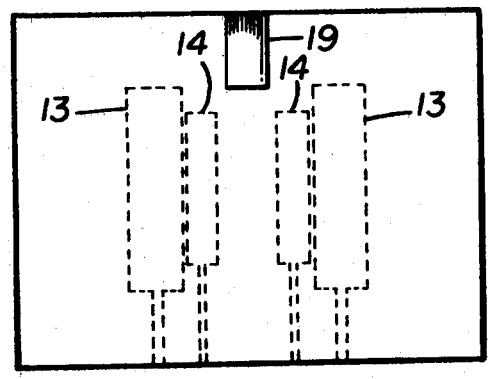
Figure 3C:
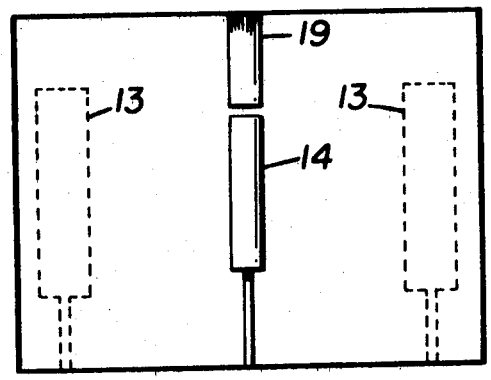

With reference to FIGS. 3(a), (b) and (c), when the movable post 19 is directly above the front vertical stationary post 13, both the posts 19 and 13 are sharply in focus as indicated by the solid lines. However, the back vertical post 14 is not sharply in focus and the viewer will see two images of the post spaced equidistance on either side of the posts sharply in focus. The double images of the back vertical post 14 are indicated by the dotted lines. However, when the vertical post 19 is approximately halfway between the two stationary posts 13 and 14, only the movable post 19 remains sharply in focus—that is, if the patient maintains his binocular focal plane at the movable vertical post 19. As shown in FIG. 3(b), the viewer will be able to perceive dual images of both the front stationary vertical post 13 and the back stationary vertical post 14. The dual images are indicated by the dotted lines. Ultimately, as shown in FIG. 3(c), the movable post 19 ends its travel over the back vertical post 14. Both posts are sharply in focus. However, there is a widely spaced dual image of the front vertical post 13 indicated by the dotted lines.

Images similar to that illustrated in FIG. 3(b) could be drawn for each intermediate point as the movable post 19 moves from the front vertical post 13 to the back vertical post 14 and back again to the front vertical post. It may be advantageous in some cases to place an attention-getting symbol, image or mark on the movable post 19 in order to fixate the patient's attention on that post.

In a similar fashion, the stationary posts 13 and 14 could be colored differently to enable to the patient to make a better subjective evaluation of the various images perceived. The patient's subjective perception of the images perceived could then be compared to that image which ought to have been perceived by a person having proper binocular vision without any disabilities. In this fashion, persons having binocular vision disorders can be initially discovered or diagnosed and the nature of the disability parameterized. Then the binocular vision device can be utilized both to measure the progress of any particular therapy or treatment utilized for correcting binocular vision disabilities and as a therapeutic exercise device itself.

The described binocular vision device can be equipped with features that are state of the art in opthalmology. For example, a mechanism can be utilized in combination with the viewing aperatures 12 to occlude the interior of the enclosure. Also, a hood 31 (see FIGS. 1 and 2) can be utilized to block distracting visual events occuring outside of the enclosure from the patient's view. Also, an adjustable chin rest 32 may be mounted below the viewing aperatures 12 for enhancing the stability of the patient's head as he views the interior of the enclosure 11. The device could be made more versatile by including means for changing the distance between the stationary vertical posts 13 and 14 on the carriage 16. The vertical distance between the top of the stationary posts 13 and 14 and the bottom of the movable posts 19 may also be adjusted, for example, using a nut 33 and a threaded shaft 34 securing the post 19 to the horizontal support 21.

The invented binocular vision device has been described in context of schematic and representative embodiments. Many variations, substitutions and modifications can be made to the described device, including the absolute or relative dimensions of the parts, materials used, and the like without departing from the spirit and the scope of the invention as described in the appended claims.

I claim:

1. A device for testing, exercising and enhancing binocular vision comprising in combination,
   (a) An enclosure having a pair of viewing apertures spaced for registry with human eyes through which an interior display space within the enclosure may be viewed,
   (b) A first stationary element oriented and positioned in a vertical plane equidistant from each aperture within the display space,
   (c) A second stationary element oriented in the same vertical plane as the first element positioned a linear distance from the first element within the display space,
   (d) A focus element oriented in the same vertical plane as the stationary elements above the stationary elements within the display space,
   (e) Means for moving the focus element back and forth in the vertical plane from above one stationary element to above the other, and
   (f) Means for moving the focus element up and down in the vertical plane varying the vertical spacing between the respective stationary elements and the focus element.

2. The device of claim 1, further including means for uniformly illuminating the display space within the enclosure.

3. The device of claim 2, further including means for adjusting the distance between the first and second stationary element in a range from 25 centimeters to 50 centimeters.

4. The device of claim 2, further including means for linearly moving the stationary elements within the display space toward and away from the viewing aperatures.

5. The device of claim 2, wherein the focus element includes an attention-focusing symbol.

6. The device of claim 2, wherein the first stationary element is one color, the second stationary element a second color.

7. The device of claim 2, wherein the means for moving the focus element comprises in combination:
   (a) A belt,
   (b) A plurality of pulleys receiving the belt orienting it to move linearly in a plane parallel to the vertical plane of the first, second, and focus elements, (c) A horizontal support member secured at one end to the belt extending perpendicularly therefrom across the display space,
(d) A frame member supporting the distal end of the horizontal support member also oriented parallel to the vertical plane of the first, second and focus elements, the focus element being secured to and appending from the horizontal support member, and
(e) Means for moving the belt.

8. The device of claim 7, wherein the means for moving the belt includes:
(a) A shaft having one end keyed to one of the pulleys,
(b) A bearing supported by the enclosure receiving and supporting the shaft, the shaft extending through the bearing to outside the enclosure, and
(c) A hand crank keyed to the end of the shaft exterior the enclosure, whereby rotating the hand crank drives the pulley keyed to the shaft and moves the belt within the enclosure.

9. The device of claim 7, wherein the distal end of the horizontal support member includes a wheel freely rotatable about an axis parallel to the horizontal support, and wherein the frame member supporting the distal end of the horizontal support member defines a channel for receiving and supporting said wheel.

10. The device of claim 7, further including a plurality of interior wall structures defining the display space for preventing the horizontal supports, the pulleys, the belt, and other mechanisms within the enclosure exterior the display space from being observable through the view aperatures.

11. The device of claim 2, further including a chin stop mounted exterior the enclosure below the view aperatures and means for adjusting the chin support up and down relative to the view aperatures.

12. The device of claim 2, further including a hood mounted exterior of the enclosure for preventing external visual stimuli from distracting a person viewing the interior display space.

* * * * *